United States Patent
Onda et al.

Patent Number: 6,107,084
Date of Patent: Aug. 22, 2000

[54] METHOD FOR THE PREPARATION OF AN IMMOBILIZED PROTEIN ULTRATHIN FILM REACTOR AND A METHOD FOR A CHEMICAL REACTION BY USING AN IMMOBILIZED PROTEIN ULTRATHIN FILM REACTOR

[75] Inventors: Mitsuhiko Onda, 1560-8, Kokubumachi, Kurume-shi, Fukuoka-ken; Yuri Lvov; Katsuhiko Ariga, both of Kurume; Toyoki Kunitake, Fukuoka-ken, all of Japan

[73] Assignees: Mitsuhiko Onda, Fukuoka-ken; Japan Science and Technololy Corp., Saitama, both of Japan

[21] Appl. No.: 08/730,929

[22] Filed: Oct. 16, 1996

[30] Foreign Application Priority Data

Oct. 19, 1995 [JP] Japan .................................. 7-270814

[51] Int. Cl.⁷ .............................. C12M 1/00; G01N 1/04; G01N 33/53
[52] U.S. Cl. ..................... 435/289.1; 356/244; 427/2.13; 427/414; 435/7.1; 435/299.1; 435/287.9; 436/518; 436/810
[58] Field of Search .......................... 356/244; 427/2.13, 427/414; 435/7.1, 299.1, 287.9, 289.1; 436/518, 810

[56] References Cited

U.S. PATENT DOCUMENTS

| | | | |
|---|---|---|---|
| 5,063,081 | 11/1991 | Cozzette et al. | 427/2 |
| 5,521,702 | 5/1996 | Salamon et al. | 356/244 |
| 5,643,721 | 7/1997 | Spring et al. | 435/6 |

OTHER PUBLICATIONS

Lvov et al. "Assembly of multicomponent protein films by means of electrostatic layer–by–layer adsorption" JACS, vol. 117, No. 22, pp. 6117–6123, 1995.

Lvov et al. "Layer–by–layer assembly of alternate protein/polyion ultrathin films" Chemistry Letters, No. 12, pp. 2323–2326, 1994.

*Primary Examiner*—Jezia Riley

[57] ABSTRACT

A method for the preparation of an immobilized protein ultrathin film reactor by immersing a solid support alternately into an aqueous solution of protein, and into an aqueous solution of polyion charged oppositely to said protein and preparing a structurally controlled ultrathin film of mono- or multi- protein layers on a said solid support with precision at molecular level. And a method for chemical reaction of a substrate by preparing an immobilized protein ultrathin film reactor composed of multiple layers of protein on a solid support by above mentioned method, and initiating a chemical change of the substrate molecules using obtained immobilized protein ultrathin film reactor.

7 Claims, 6 Drawing Sheets

METHOD FOR THE PREPARATION OF AN IMMOBILIZED PROTEIN ULTRATHIN FILM REACTOR AND A METHOD FOR A CHEMICAL REACTION BY USING AN IMMOBILIZED PROTEIN ULTRATHIN FILM REACTOR

BACK GROUND OF THE INVENTION

This invention relates to a method for the preparation of an immobilized protein ultrathin film reactor which can cause substrate molecules to undergo chemical reactions, especially enzymatic reactions, on an ultrathin film of protein assembled on a solid support.

DESCRIPTION OF THE PRIOR ART

In bioreactions, generally, highly effective and highly selective physical and chemical processes are carried out by a sole or a co-operative functionality or by linked functions of proteins such as enzyme. To imitate these functions artificially, i.e. to develop a new molecular device such as an enzyme reactor or a bio-sensor, it is necessary to use a multilayered protein structure, which has been assembled in an appropriate order. Method for immobilizing protein molecules on a solid support are roughly classified as follows; i) The protein is immobilized directly on a substrate by means of adsorption or casting, ii) The protein is transferred as a thin film from the surface of liquid, e.g. Langmuir-Blodgett method (LB method) and iii) Proteins are immobilized by alternate adsorption with other components.

When applying the method in which a protein is adsorbed directly to a substrate, the thickness of the protein layer is restricted to the region where the interaction with the solid substrate is effective. Therefore, it is difficult to repeat the adsorption of protein using this method, and the assembly of multi-component protein films with an imposed order is still not possible.

In the casting method either an aqueous solution of the protein itself, or a mixture of an aqueous solution of the protein and a biomolecule can be cast. Their lipid layer is cast on a solid support, immobilizing the protein molecules and the solvent is then evaporated. By this method it is also difficult to immobilize the multiple species of protein in a desired order.

As a precise preparatory method for assembling thin film of molecular layers in a pre-determined order, the LB method is widely used. This method is characterized as follows. A substance which has high solubility, such as a lipid, is dissolved into an organic solvent and the solution is spread over the surface of water, then the thin film obtained is transferred on a solid substrate. The order of the assembled films and their thickness can be controlled. However, since typical protein has a tendency to denature and lose activity at the air-water interface, this method is not widely applied to most species of protein. Further, in this method proteins are readily lost by scattering in the water phase. It is therefore not an economically satisfactory method, especially when expensive proteins are used. Still further, since the LB method has problems such as less productivity, instrument with expensive equipment and difficult handling, this method is not recognized as a popular method for immobilizing proteins.

Recently, to minimize the denaturation of protein the following method is proposed ; An enzyme coated by a lipid or the like is dissolved into an organic solvent and then a necessary amount is spread to water. A feature of films obtained by this method is the dense packing of the lipid molecules which interferes with substrate diffusion into the film. Therefore, this method is not suitable for use of an enzymatic reaction system. There is a report which claims that in the case where an LB film is used to immobilize glucose oxidase (GOD), the difficulty of diffusion of substrates or products hinders the progress of reaction process. LB film assembly is generally restricted to a flat and non-porous support, and it is not recognized as a suitable method for immobilizing proteins on different types of support with various functions.

It has become possible to immobilize various species of protein in pre-determined order by adsorbing the protein alternately with the other component and by immobilizing the protein layer by layer. Recently, several concrete examples regarding this method have been reported. The accumulation of multiple (two) species of protein by using a specific ligand such as biotin/avidin is well known as one of the concrete examples of this method. However, this requires the protein to be labelled with considerable effort, and since this method can be applied only for restricted combinations of protein, it can not be said to be a widespread method. Further, the method to adsorb protein alternately by electrostatic interaction with ruthenium phosphate or bolaamphiphiles is proposed. However, since the connecting component between protein is too rigid in this method, the number of layers to be assembled is limited to few and the proteins to which it can be applied are restricted to a specific species. Namely, by said methods, it is difficult to immobilize the necessary species of protein in pre-determined order, these methods are not suited for the preparation of enzymatic reaction system which uses multiple species of protein.

Sill further, a report has been published recently, which discloses a method to immobilize protein by using a product produced by bonding a rigid surfactant-like substance called boladication (which is cationic at both ends and can bind with an anionic protein) (J. Chem. Soc., Chem. Commun., 1994, 1297–1298). Since baladication is too rigid, its substrate can not be penetrated easily into a protein matrix. Therefore, this method is recognized as having a defects. Firstly, the reactor produced have a slow reaction velocity with a reactive substrate, and secondly the proteins which can be immobilized by using baladication are restricted to anionic protein.

OBJECT OF THE INVENTION

The inventors of this invention have conducted intensive study to improve the defects of conventional methods and to find a method to immobilize and assemble multiple species of different proteins in a desired order, without accompanying denaturation of the protein molecular layer, and to initiate a chemical reaction with substrate molecules, and consequently accomplished the present invention. That is, the inventors found that the ultrathin protein film assembled in a pre-determind order can be obtained regardless of the species of protein, by assembling the protein under conditions where protein is charged, e.g. at pH conditions far from the isoelectric point. Thus, the object of this invention is to provide a method for the preparation of an immobilized protein ultrathin film reactor which initiates chemical reactions of substrate molecules, especially enzymatic reactions. And another object of this invention is to provide a method for a chemical reaction by using an immobilized protein ultrathin film reactor produced by a method according to this invention.

BRIEF SUMMARY OF THE INVENTION

The above mentioned object is accomplished by a method for preparation of an immobilized protein ultrathin film reactor comprised of immersing a solid support alternately into an aqueous solution of the protein and into an aqueous solution of an organic polyion which is charged oppositely to said protein, and preparing a structurally controlled ultrathin film of protein having precision at a molecular level on said solid support. The above mentioned object is also accomplished by a method for the preparation of an immobilized protein ultrathin film reactor comprising the steps of immersing a solid support with electrically charged surface into an aqueous solution of oppositely charged polyion or protein to said support to reverse the surface charge by neutralization and resaturation, then immersing the solid support with electrically charged surface into an aqueous solution of a new oppositely charged polyion or protein to said support to reverse the surface charge by neutralization and resaturation, by repeating said steps, and preparing an ultrathin film in which at least two proteins are assembled.

And another object of this invention is accomplished by a method for a chemical reaction of substrate molecules comprising the step of preparing an immobilized protein ultrathin film reactor composed of multiple layers of protein on a solid support using the above mentioned methods, and initiating a chemical change of substrate molecule using obtained immobilized protein ultrathin film reactor. Further, the said object is accomplished by a method for a chemical reaction of substrate molecule comprising by immobilizing a protein thin film on a support having a separating function and separating a substrate and products of the chemical reaction, and the said method wherein the protein is an enzyme.

BRIEF DESCRIPTION OF DRAWINGS

These objects of the present invention will be clarified by the following description of preferred Examples of the present invention with reference to the accompanying drawings, wherein.

DETAILED DESCRIPTION OF THE INVENTION

Figure 1:
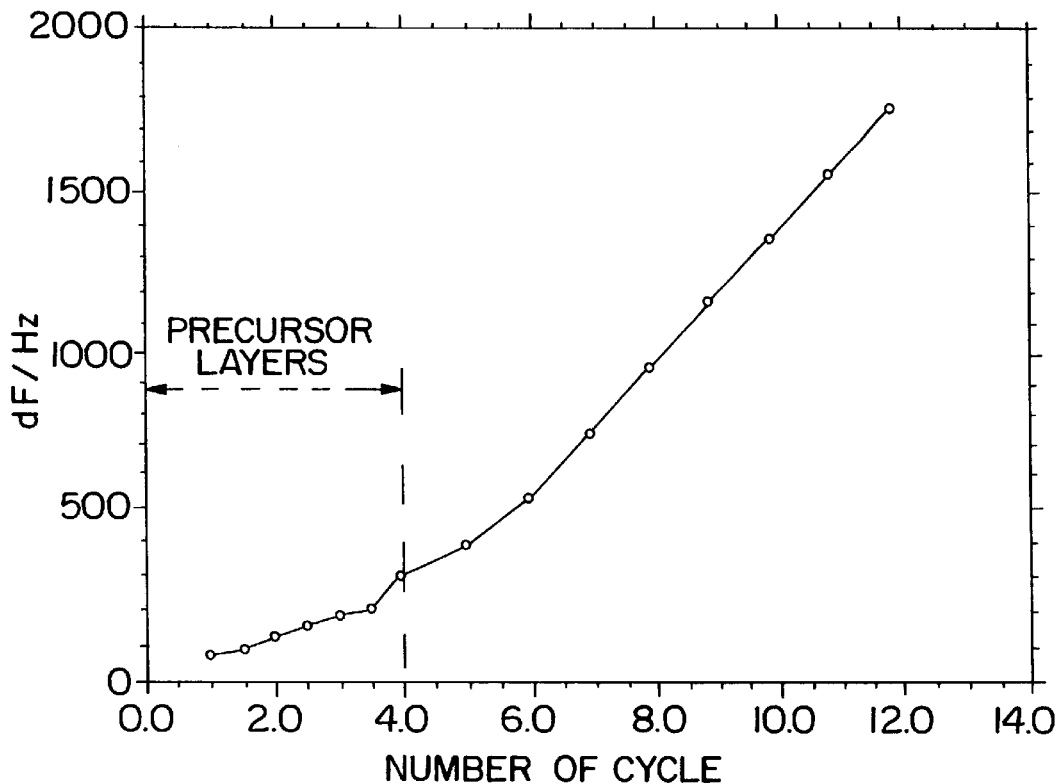
FIG. 1 is a graphical representation indicating frequency changes of quartz crystal microbalance based on time progress of protein adsorption of Example 1.

In this invention, it is possible to prepare an ultrathin film of protein molecules having a pre-determined number of layers and a molecular level thickness, while maintaining the original activity. The preparation of said ultrathin film is based on the following theory. When a solid support which bears opposite charge to the protein is immersed into an aqueous solution of the protein, the protein is adsorbed to the surface of the solid support by means of electrostatic interactions. On this occasion, the protein not only neutralizes the charged surface of the support, but also adsorbs excessively, and then, the surface is recharged oppositely. Then, this is immersed into aqueous solution of oppositely charged polyion to said protein. Consequently a new opposite charge appears on the surface by means of neutralization and excess adsorption of the polyion. This process, of alternate adsorption of a protein and a polyion can be continued infinitely. The quantity of excess adsorption at each step is restricted by saturation of the charge, thus a constant quantity of protein or organic polyion can be immobilized at each step.

As clearly illustrated in the above mentioned preparation theory, it is possible to use a solution of protein in it's natural state, the degeneration of protein can be avoided. Considering that the conventional well-known methods for the immobilization of proteins occasionally causes a degeneration of the protein, thereby hindering protein activity, it can be said that the method for immobilization of protein of this invention is an excellent method for the preparation of an enzymatic reactive system.

Further, considering that the adsorption of the protein is based on electrostatic interactions and every protein has some surface charge, this method can be said to be a method which can be widely applied to water soluble proteins. Since the surface charge of proteins can be controlled by the pH of a solution, by selecting an aqueous solution of protein of appropriate pH, and a suitable polyion bearing opposite charge, the immobilization of many species of protein is possible. This means that the present invention is not limited to the preparation of enzymatic reaction systems for special reactions, but can be widely applied to the ordinal reactions.

Further, according to the present invention, it is possible to immobilize multiple species of protein in a predetermined order and to prepare a composite enzymatic reaction system having an excellent reactivity by combinations of different protein functionalities.

Still further, since the soft polyion used to immobilize the protein can alter its conformation to suit the shape of the protein molecule, the diffusion of a substrate or products in the film is very easy in comparison with the case of a rigid component such as lipid. This is another considerable advantage of this invention over those made from rigid component.

And, the method for the preparation of protein thin film of the present invention, is carried out in a short time by a simple process characterized only by immersing a support into an aqueous solution of protein or organic polyion, and also does not need special equipment. Therefore, many different types of solid support can be selected, and additional functions such as separating function can be added to the enzymatic reaction system.

The present invention is more concretely illustrated below. The organic polyion of this invention indicates a polymer with electrically charged functional groups in its main or side chain. In general, as the polyanionic compounds having a functional group which is negatively charged e.g. sulfonic acids, sulfuric acids and carboxylic acids can be mentioned, and as the concrete examples sodium polystyrenesulfonate (PSS), sodium polyvinylsulfurate (PVS), sodium dextransulfurate, sodium chondroitinsulfurate, polyacrylic acid (PAA), polymethacrylic acid (PMA), polymaleic acid and polyfumaric acid can be used. As polycationic compounds having a functional group which is positively charged e.g. quaternary ammonium groups and amino groups can be mentioned, and as the concrete examples polyethyleneimine (PEI), polyacrylamine hydrochloride (PAH), polydiallyldimethylammonium chloride (PDDA), polyvinylpyridine (PVP) and polylysine can be used. All these organic polyions are characterized as water soluble or soluble in a mixture of water and organic solvent. And, it is also possible to use electric conductive polymers, functional polyions such as poly(aniline-N-propanesulfonic acid) (PAN), several types biopolymers of deoxyribonucleic acids (DNA) and ribonucleic acids (RNA), and charged polysaccharide biopolymer such as pectin.

Generally, since the surface of any water soluble protein is electrically chargeable, they can be used in this invention irrespective of other characteristics. For instance, glucoseoxidase (GOD; molecular weight 186000, isoelectric point 4.2), peroxidase (POD; molecular weight 42000, isoelectric point 7.2), glucoamylase (GA; molecular weight 100000, isoelectric point 4.2), alcohol dehydrogenase (ADH; molecular weight 100000, isoelectric point 9), diaphorase (DA; molecular weight 700000, isoelectric point 4), cytochrome (Cyt; molecular weight 12400, isoelectric point 10.1), lysozyme; (Lys; molecular weight 14000, isoelectric point 11), histone f3 (His; molecular weight 15300, isoelectric point 11), myoglobin (Mb; molecular weight 17800, isoelectric point 7.0) and hemoglobin (Hb; molecular weight 64000, isoelectric point 6.8) can be used.

As the solid support, a substance, the surface of which is electrically chargeable such as silver (anionic surface), glass, quartz (anionic surface) and surface charged polymer film, or a substance to which electric charge can be introduced such as gold (electric charge can be introduced to the surface by adsorption of mercaptopropionic acid or others) and various kinds of electrode can be used. Further, this method is theoretically based on simple adsorption, therefore, it is not necessary for the solid support for immobilization to be flat, and various materials can be selected for the solid support. For instance, in addition to a flat solid substrate, a porous solid substrate such as filter, powder of silica gel or resin marbles can be used.

Basically, protein and polyions are used in aqueous solution, however, organic solvents can be mixed therewith in varying proportions. The concentration of each solution depends on the solubility of the protein and the organic polyion, and since the adsorption procedure is based on the neutralization and resaturation of an immobilized charge, it is not necessary to prepare the concentration strictly. Typical concentrations are, 1 mg/ml is indicated for the solution of protein and 1–3 mg/ml is indicated for the solution of organic polyion. However, it is not intended to be limited in this range. And, the pHs of the solution are adjusted to the pH level where the protein or polyion is charged sufficiently, by adding aqueous HCl or by using a buffer.

At the first step, a solid support the surface of which is electrically charged is alternately immersed into the solution of two types of organic polyion (polycation and polyanion), by doing this a flexible thin layer of the polyion is immobilized on the surface of said solid support. If this immobilizing procedure for the thin layer of the polyion is omitted, the followed preparation of ultrathin film of protein is not always possible. The thin film of polyion being charged oppositely to the protein which is the final adsorbent is immobilized to the outermost surface. Then, the procedure of immersing in an aqueous solution of protein, washing by water, immersing in an aqueous solution of polyion and washing by water is repeated and the ultrathin film of protein multilayer is prepared. The normal immersion period is about 10–20 minutes, however, in this procedure, since an adsorption equilibrium can be obtained, the strict setting up of immersing period is not required.

When the ultrathin film of the protein prepared by the above mentioned procedure is applied as an enzymatic reaction system, it is necessary to immerse a solid support on which a thin film is immobilized into an aqueous solution containing the substrate, but special equipment for such a preparation is not required. Further, the reaction can be initiated by making an aqueous solution of the substrate pass through a porous support on which a thin film of protein is immobilized.

EXAMPLES

The present invention will be more clearly understood with reference to the following Examples.

Example 1, 2

As the Example 1 and 2, immobilization experiments are carried out to confirm that the layers of protein are immobilized repeatedly and constantly layer-by-layer. On the surface of a quartz crystal microbalance coated by a silver electrode, a protein ultrathin film is immobilized. The quartz crystal microbalance is well-known as a microbalance, and is a device which can estimate the immobilized mass to a level of precision of $10^{-9}$ g by means of measuring frequency shifts. The surface of the silver electrode (surface area is about 0.2 cm$^2$) is negatively charged because of a partial oxidization. At the first step, a few precursor layers of polycation and polyanion are alternately immobilized on the silver electrode quartz crystal microbalance, and then a protein is absorbed on said surface. In Example 1, the mass of the alternate adsorption of PSS and POD is estimated, and that of PEI and GOD is estimated as the Example 2. FIG. 1 shows the frequency changes of the quartz crystal microbalance based on the adsorption of Example 1. As indicated by FIG. 1, the adsorption mass of each layers upon repeated adsorption is almost constant except for the first few layers. That is, this result indicates that, according to this invention, the adsorption of protein of a constant mass can be observed at each immobilization. And, the mass of protein adsorption at each immobilization step is calculated to correspond the adsorption of a single molecular layer of protein. Further, from FIG. 1, it is also recognized that these alternate adsorption procedures can be repeated over and over, until the number of layers, corresponds to that required for an enzymatic reaction system.

Example 3, 4

Figure 2:
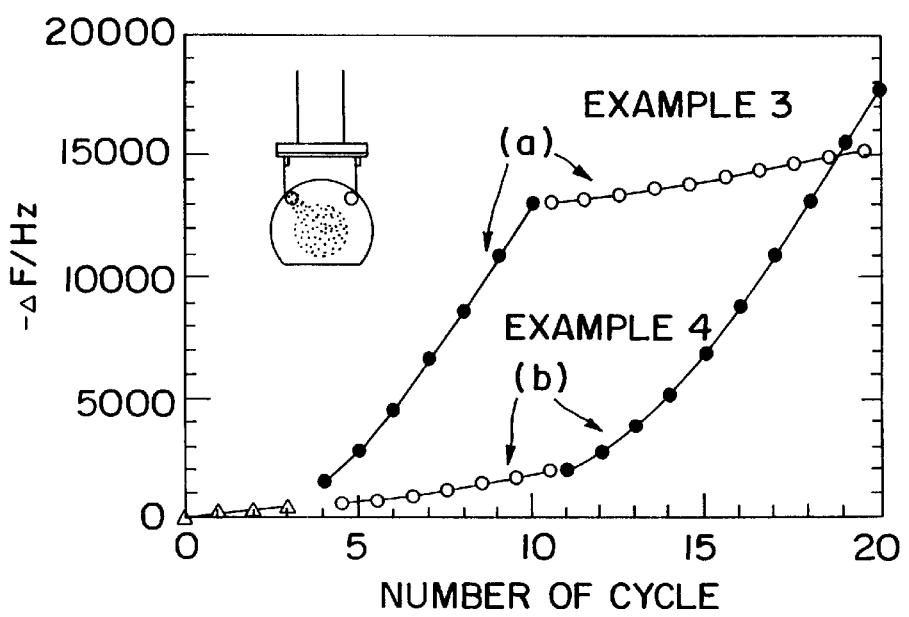
FIG. 2 is a graphical representation indicating frequency changes of quartz crystal microbalance based on time progress of protein adsorption of Example 3 and 4.

As the Example 3 and 4, multiple species of protein are immobilized in one thin film. In Example 3, a thin film composed by alternate layers of PEI and GOD is prepared on a precursor layer, then PSS and POD are alternately absorbed onto said thin film. And as Example 4, the two species of protein from Example 3 are assembled in the reverse order. That is, in Example 4, a thin film composed by alternate adsorption of PSS and POD is prepared on a precusor layer, then PEI and GOD are alternately absorbed onto it. The results obtained are shown in FIG. 2. As clearly indicated in this figure, the process for the preparation of each protein layer is not affected by the process for preparation of another protein layer, and the frequency change of the corresponding part of Example 3 and 4 is the same. This fact shows that protein layers can be prepared independently, indicating that protein layers can be assembled in a pre-determined order.

This is a very important knowledge for the development of an excellent enzymatic reaction system which has high reactivity to a continuous chemical change.

Example 5

Figure 3:
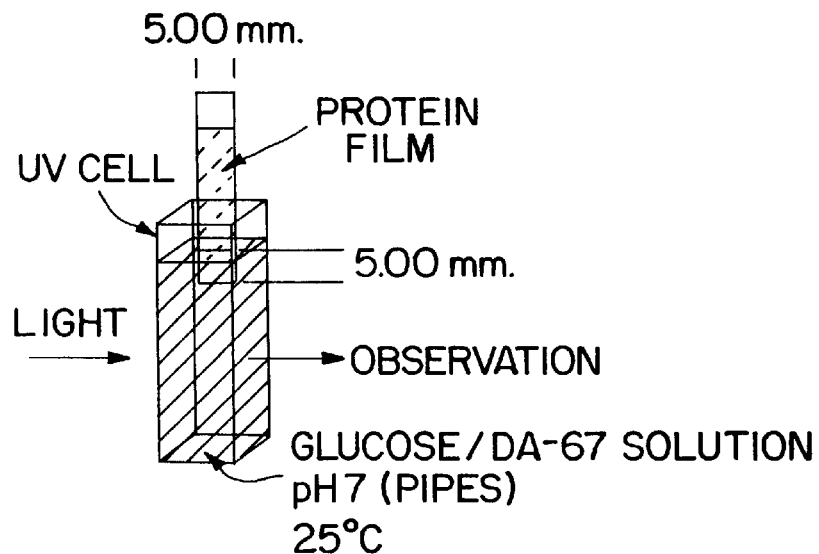
FIG. 3 is a schematic view of measuring apparatus of Example 5.
Figure 4:
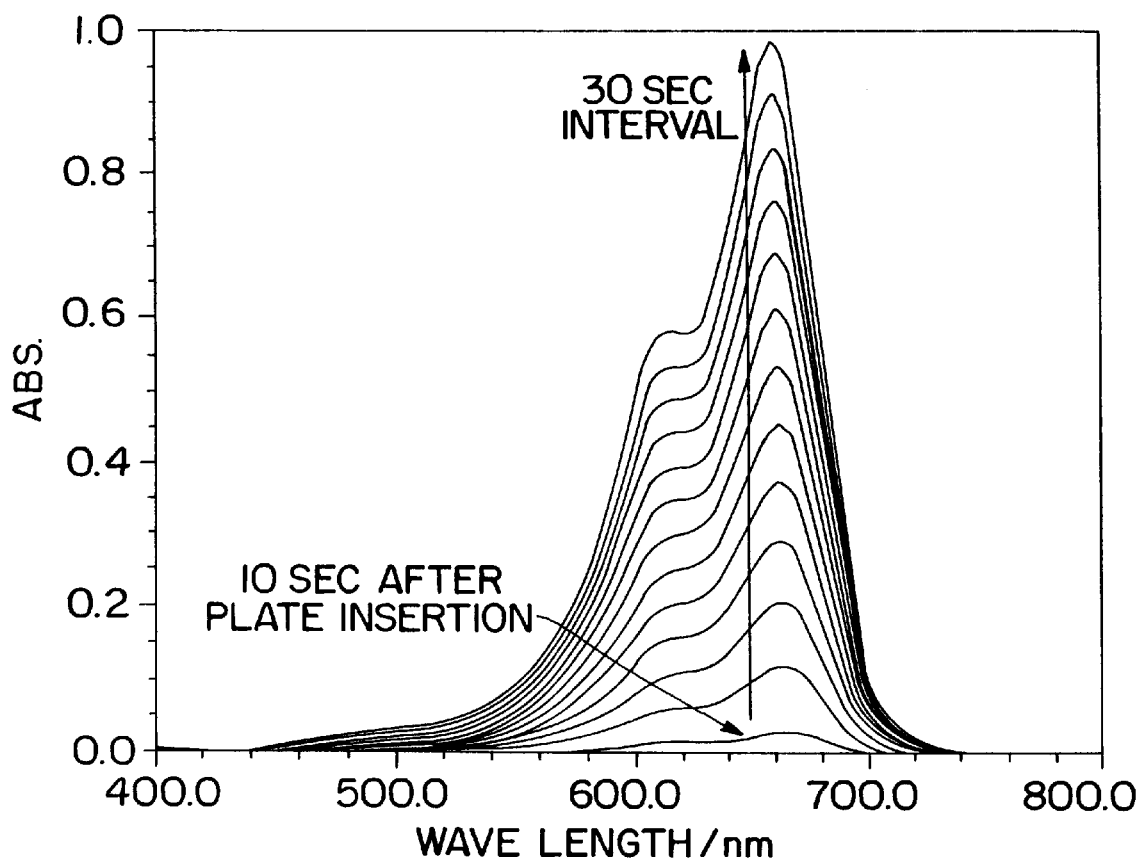
FIG. 4 is a graphical representation of UV specta of Example 5.

In Example 5, a protein thin film composed of a single layer of GOD single layer is prepared. This thin film is immersed into an aqueous solution including glucose, POD and redox dye DA67, and an enzymatic reaction is initiated. The chemical reactions are indicated in the following reaction formula and the schematic representation of measuring system is illustrated in FIG. 3. As the reaction progresses, DA67 is oxidized and an adsorption increase is detected at 607 nm and 665 nm. FIG. 4 shows the spectral changes of this Example. With the progress of a time, these adsorption peaks increase quickly indicating that the reaction is proceeding smoothly through the medium of the activity of GOD immobilized in the thin film, and also to indicate that the GOD maintains it's activity.

D), because of the absence of GOD in the solution. These results indicates that GOD molecules do not leak into the solution during the first immersion step of the GOD immobilized thin film (Example 7), proving the stability of immobilized GOD in the thin film. As Example 9, the GOD immobilized thin film is immersed into an aqueous solution (of glucose, POD, and DA67). This process is repeated twice That is, at step D of FIG. 5 the thin film is immersed and removed at step E. It can be clearly understood from the observation of FIG. 5, that the adsorption increase is detected only in the presence of the GOD thin film, and when the thin film is removed from the solution, adsorption does not increase. This fact clearly illustrates that the observed adsorption increase is based on the catalyzed reaction by GOD. This experiment is repeated twice and the results show a similar adsorption increase. Consequently, the possibility for recycling the GOD thin film is clarified. Finally, as Example 10, a GOD immobilized thin film (double layered film) is prepared separately, and it is immersed into the same aqueous solution of substrate (FIG.

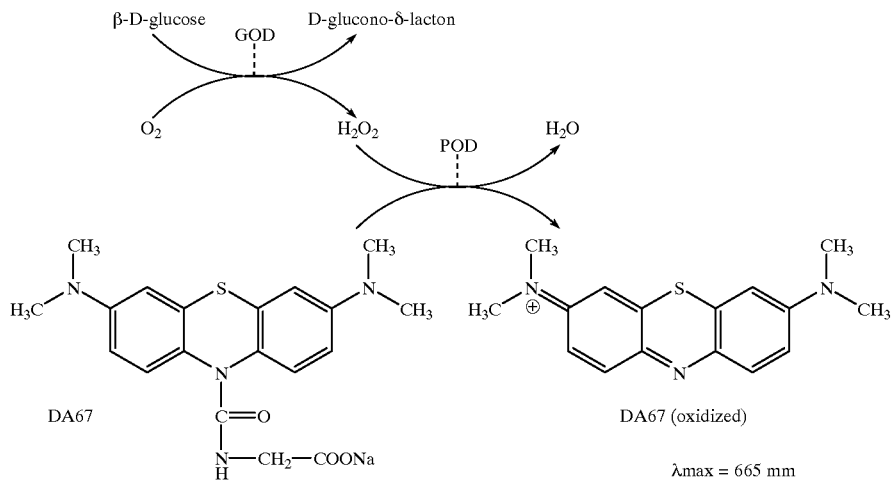

Example 6–9

Figure 5:
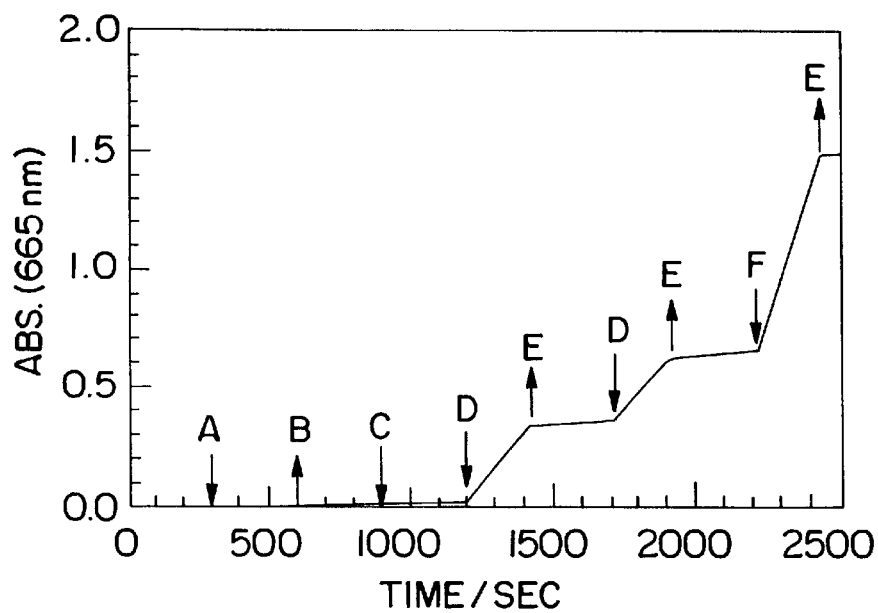
FIG. 5 is a graphical representation indicating adsorption changes of Example 6–10.

In Examples 6–9, a GOD immobilized thin film (single layered film) is prepared in a similar way to that in Example 5. Said thin film is immersed into many kinds of solution, and confirmed that the spectral changes shown in FIG. 4 are based on the reaction catalyzed by immobilized GOD. These results are summarized in FIG. 5. In FIG. 5, the monitoring results of adsorption monitored at 665 nm are indicated. In Example 6, a solution of POD (0.0004 mg/ml) and DA67 (0.0001 mg/ml) is incubated for five minutes (FIG. 5, from step 0 to A). During this period, no adsorption increase is detected, and it is confirmed that the spontaneous oxidization of DA67 does not affect to the adsorption increase. Then, the GOD immobilized thin film is immersed (Example 7, FIG. 5 from step A to step B) into the solution. At this step also, no adsorption increase is detected, indicating that the spontaneous oxidization of DA67 can still be ignored. This is explained by the absence of glucose which is a substrate of GOD in the solution. It is clearly understood that the whole reaction (FIG. 3) can not be initiated, unless an oxidization of glucose by GOD is initiated. As the next step, after the removal of GOD immobilized thin film from the solution (FIG. 5 step B), 0.01 mg/ml of glucose is added to the solution (Example 8, FIG. 5 step C). An absorption increase is scarcely detected at this period (FIG. 5, step C to 5, step F). In this case, a rate which is twice as rapid as that observed from the single layered film at Example 9 is observed, indicating that the reaction rate is proportional to the number of layers of GOD in the thin film. This result also indicates that even the GOD immobilized in the innermost layer and far from the surface of the support participates with the reaction.

Example 10–15

Figure 6:
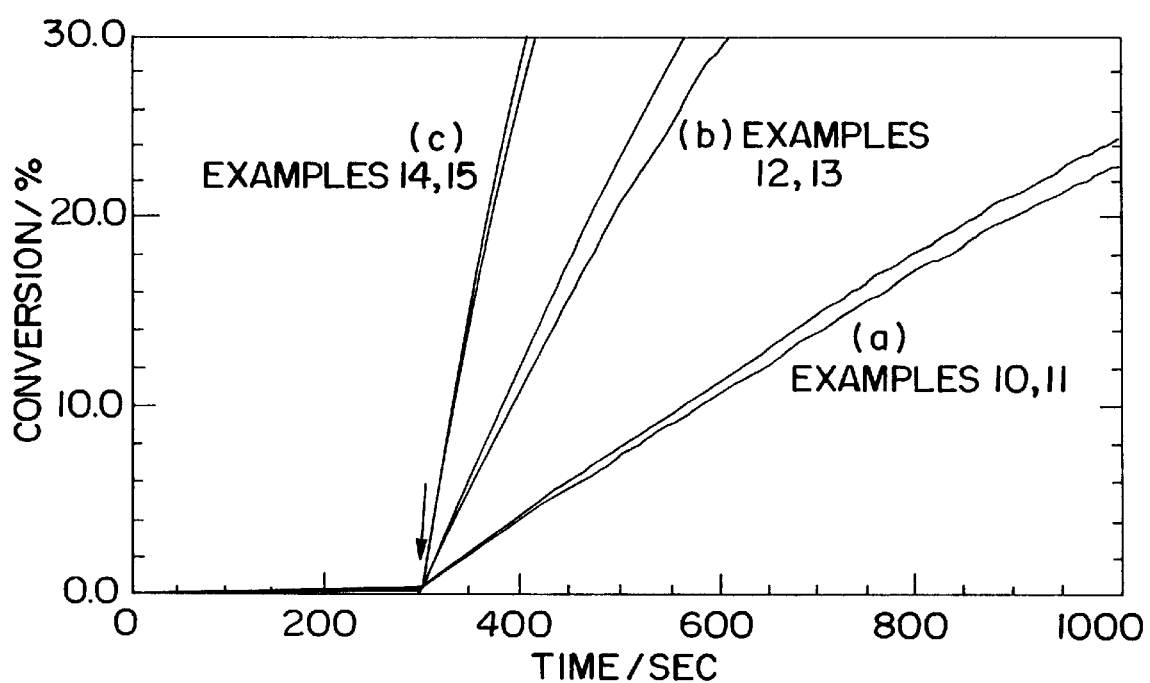
FIG. 6 is a graphical representation of changes in conversion of Example 10–15.
Figure 7A:
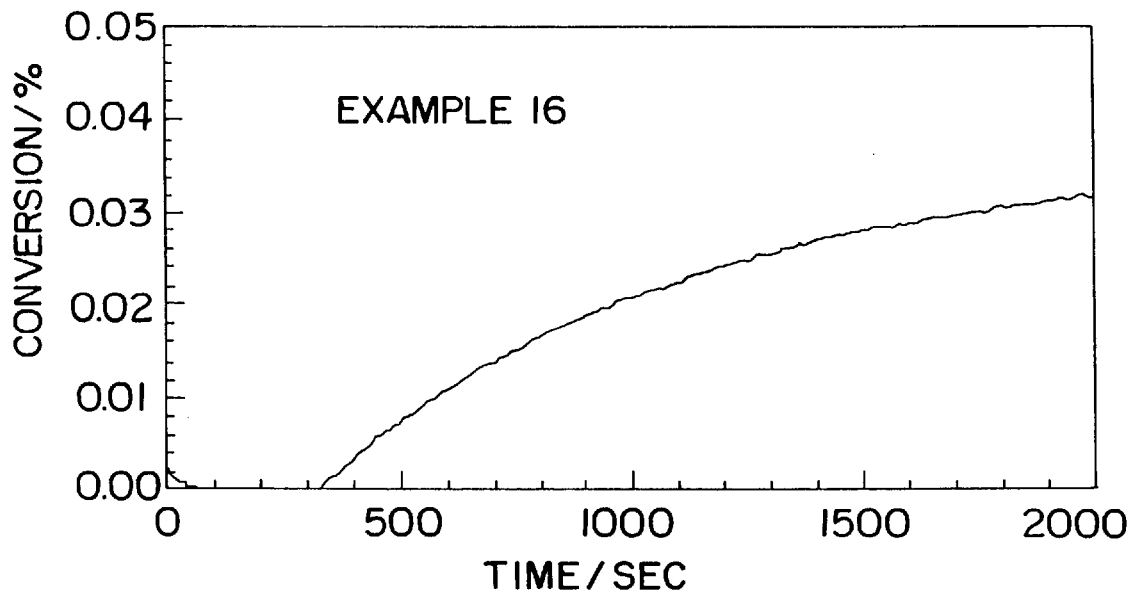
FIG. 7 is a graphical representation of changes in conversion of Example 16 and 17.
Figure 7B:
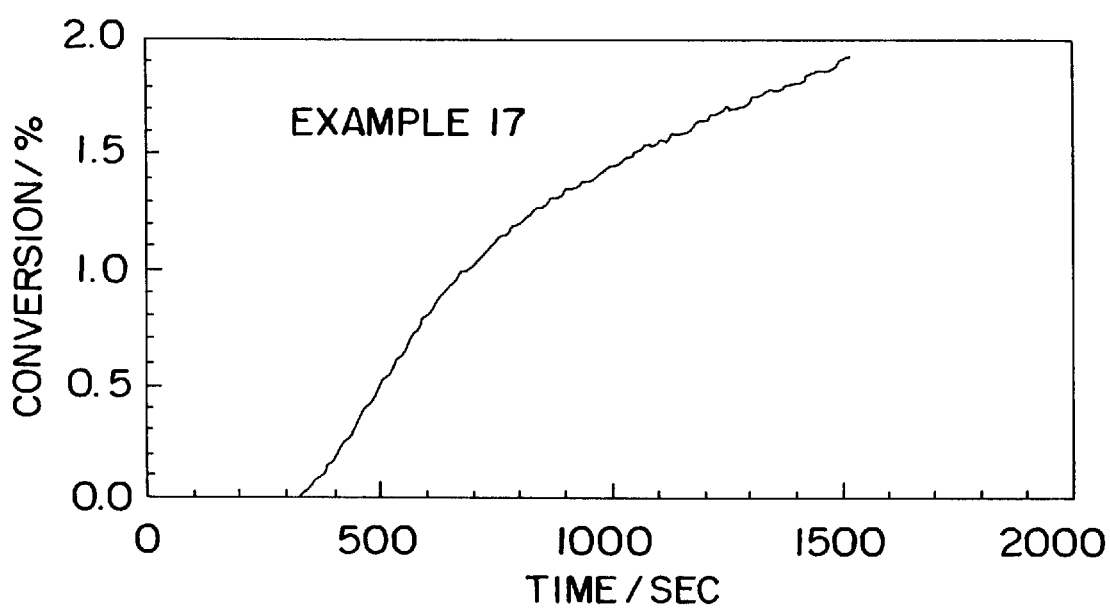

The following experiments are carried out as Example 10–15. A single layered GOD immobilized thin film (Example 10 and 11), a double layered GOD immobilized thin film (Example 12 and 13) and a triple layered GOD immobilized thin film (Example 14 and 15) is immersed into an aqueous solution of glucose (0.01 mg/ml), POD (0.0004 mg/ml) and DA67 (0.004 mg/ml), and the reaction rate is measured. The results are shown in FIG. 6, wherein the conversion is represented on the vertical axis. Two experiments are repeated under the same conditions to show good reproductivity by Example 10 and 11, Example 12 and 13, and Example 14 and 15. This good reproductivity indicates that, when this protein thin film is applied as a sensor, a precise response can be obtained. The reaction rate is obviously increased in proportion to the increase in the number of layers, when the specimens of different numbers of layers are compared. This fact shows that the GOD immobilized in the innermost layer of thin film participates fully in the reaction as shown in Example 9. The fact also indicates that the diffusion of substrate molecules or product molecules does not limit the rate. When proteins are immobilized by different methods, there are many reports disclosing that the diffusion of substrate molecules in the film limit the reactivity. The reason why said problem is solved by using the protein thin film immobilized by this method is explained as follows. Because the ions of the polyion which immobilize the protein are flexible, they do not form a high density structure and have an almost molecular thickness size, the distance for the diffusion of the substrate molecules can be essentially ignored.

Example 16

As Example 16, a POD thin film (single layered film) is prepared and immersed into a substrate solution (0.2 wt % $H_2O_2$ and 0.08 mg/ml of DA67). Progress of the reaction is shown in FIG. (7a). The conversion ratio increases with time, and an activity of POD is not lost. It is obviously understood that this reaction is initiated by a POD-catalyzed $H_2O_2$ reduction reaction.

Example 17

In Example 17, multicomponent protein assembled thin film of GOD (double layered film) laminated on POD thin film (double layered film) is prepared and immersed into an aqueous solution of glucose (0.01 mg/ml) and DA67 (0.008 mg/ml). Progress of the reaction is shown in FIG. (7b), and by the observation of this figure it is understood that the conversion increases with time. This fact indicates that a reaction can be initiated, when both GOD and POD, among the complex enzymatic reactions shown in FIG. 3, is immobilized in the thin film. That is, this fact illustrates that sequential enzymatic reactions can progress in a thin film in which multiple species protein are immobilized.

Example 18 and 19

In Example 18 and 19, thin films are prepared as in Example 5, one is stored in atmospheric condition and another one is preserved in an aqueous solution of buffer at pH7 for 2 months. After 2 months, the activity of protein is measured in a similar way to Example 5. The results obtained indicate that the protein retains almost 100% of activity in the two storage conditions mentioned above. These results indicate the long term stability of ultrathin film reaction of protein.

Example 20–22

Figure 8:
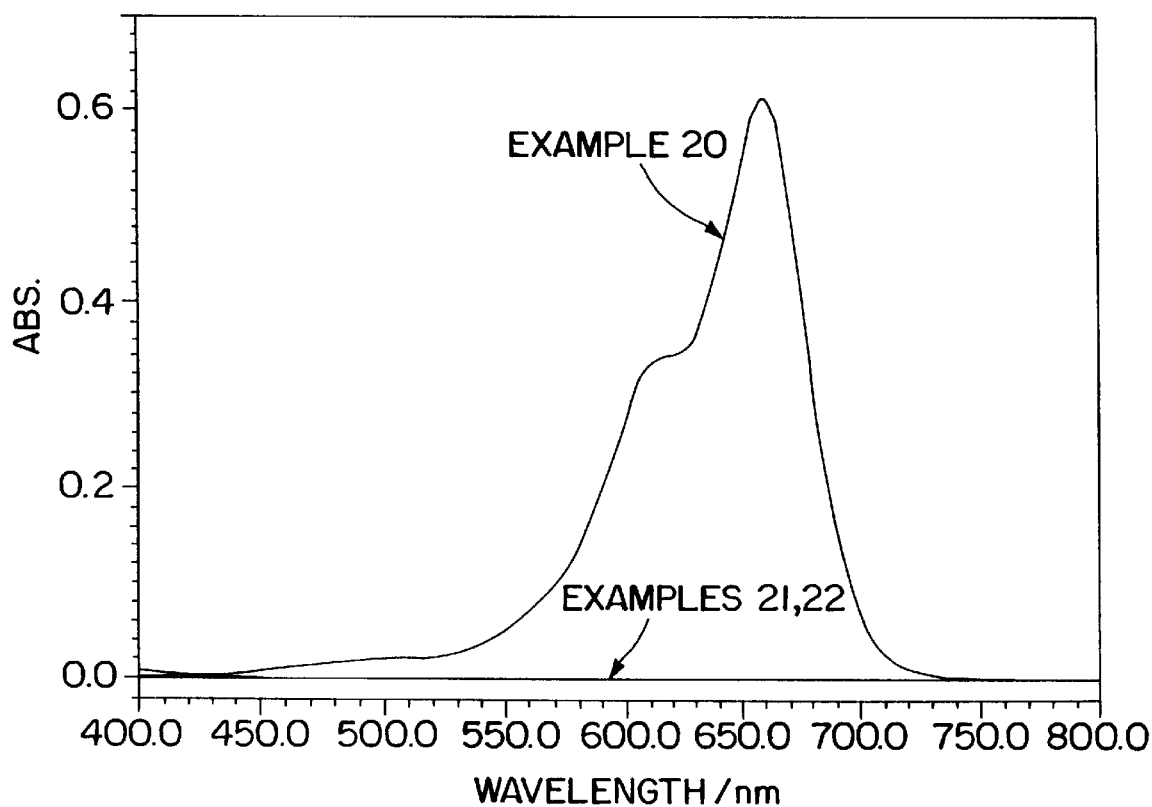
FIG. 8 is a graphical representation of UV spectra of Example 20–22.

In Example 20, a GOD thin film (four layered film) is immobilized on a porous filter, and 1 mL of 10 wt % aqueous solution of glucose is filtrated trough it. Then, POD/DA67 is added to said filtrate, and the Ultra Violet absorption spectrum is measured. The result is shown in FIG. 8. The UV adsorption which indicates the progress of reaction is recognized. That is, this Example illustrated that a porous filter can be used as a solid support for an enzymatic reaction system. In Example 21, a porous filter immersed directly into a GOD aqueous solution without using a polyion. In Example 22, a porous filter is prepared without any modification, and experiments are carried out under the same conditions as those in Example 20. The results shown in FIG. 8 indicate that the reaction does not progress at all in cases of Example 21 and 22. It can be understood that GOD is not immobilized onto a porous filter by means of the methods of Example 21 or 22, and therefore the reaction does not proceed.

Example 23–25

Figure 9:
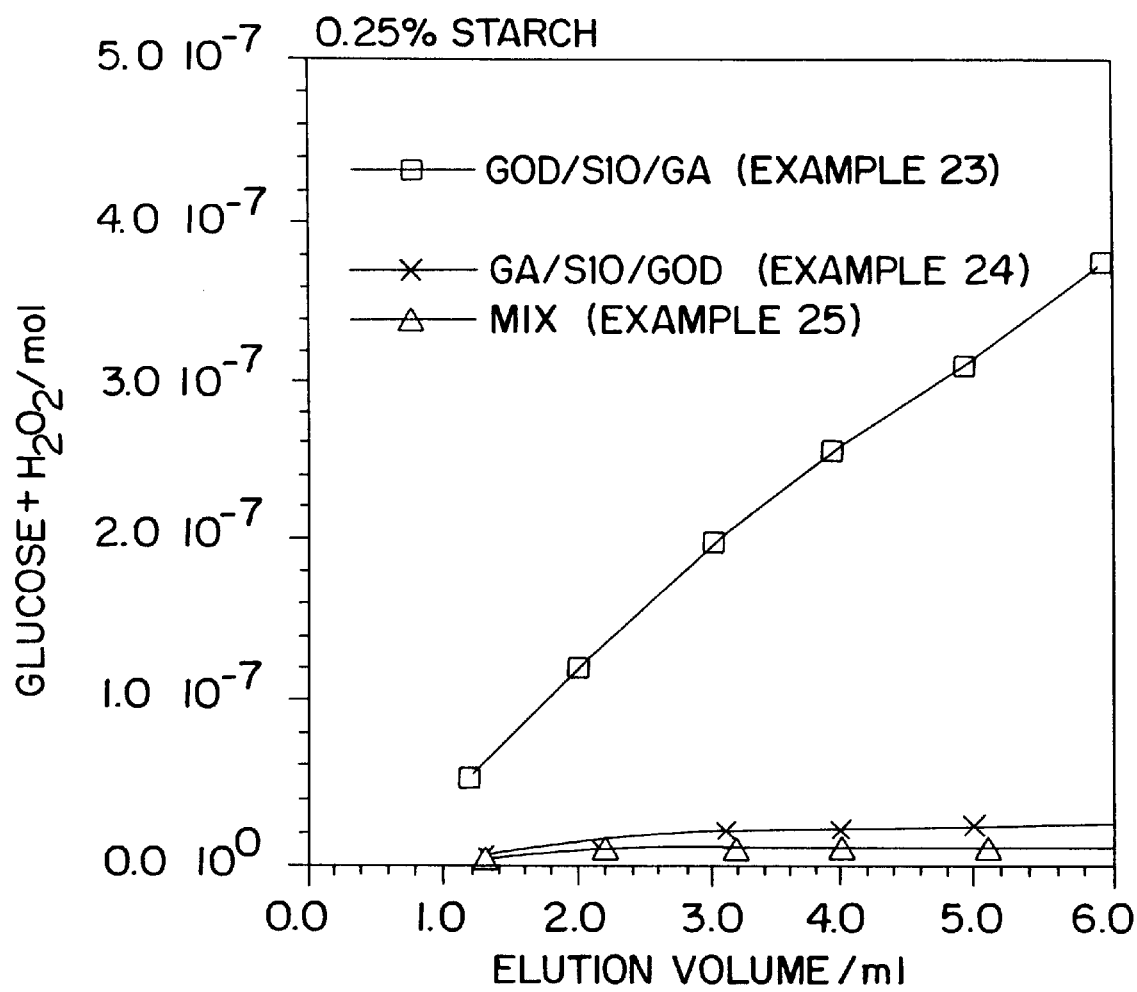
FIG. 9 is a graphical representation of amount of glucose and $H_2O_2$ generated in Example 23–25.

In Example 23, a multicomponent thin film of glucoamylase (GA) and GOD is immobilized on a porous filter, and 0.25% aqueous starch solution is filtered through it. The amount of glucose and $H_2O_2$ generated is examined (FIG. 9). GA is an enzyme which turns starch into glucose, which is a substrate of GOD. In Example 23, ten layers of alternate PEI/PSS assembly are assembled over the surface of a filter laminated with a GOD thin film precursor and a GA thin film is immobilized on the outermost layer. Example 24 is similar to Example 23, but the assembling order of GOD and GA is reversed, that is, GA is located at the inner layer on the filter and GOD layer is immobilized at the outermost surface. In Example 25, a thin film in which GOD and GA are simultaneously immobilized in one layer is prepared. The results obtained are summarized in FIG. 9, and from this figure, it is obviously that the reaction is initiated effectively only on a reactor made in the method of Example 23 which has a GA layer on it's outermost surface. This fact is explained as follows, that is, starch which is a substrate of GA comes in contact with the GA layer and generates glucose, the glucose is then oxidized by GOD located in the inner layer. On the contrary, in case of the thin film of Example 24, it can be explained that, since GA whose substrate is starch is located in inner layer, if does not have a opportunity to contact the starch and whole sequential enzymatic reaction is not initiated. Further, in case of Example 25, because only one species of protein has priority in the immobilization process, the sequential reaction which needs two species of protein is not initiated.

These results indicates that the assembly of protein thin films according to the order of reactions is indispensable for the preparation of an effective sequential enzymatic reaction system. The method for immobilization of protein as disclosed in this invention in which the assembly order of protein is controlled, differs from a conventional protein immobilization method. In the conventional method, the control of protein immobilization order is difficult. The filtrate obtained in Example 23–25, are analyzed by an iodo-starch reaction, and the results shows that the starch substrate is not detected in filtrate regardless of the progress of the reaction. This result indicates that the starch substrate polymer has not leaked to the filtrate through a porous filter which is used as a solid support. That is, in this system, the products are separated from the substrate just after the reaction.

While the Examples described are considered at present to be the preferred Examples of this invention, chemical change of a substrate molecule which is peculiar to protein is conducted with a thin film of protein as catalyst immobilized by alternate adsorption method. And, it is possible to carry out a complex enzymatic reaction in a thin film by using a thin film wherein multiple species of protein are immobilized. Further, reaction products can be separated from a substrate just after a reaction by using a porous filter as a solid support. The method of this invention is suitable for the immobilization of a wide variety of protein, and consequently it is possible to develop artificial reactors of various combinations imitating enzymatic systems or to develop new sensor systems based on the enzyme reaction.

What is claimed is:

1. A method for a chemical reaction of substrate molecules comprising immobilizing a protein thin film on a porous support by immersing a porous solid support alternately into an aqueous solution of protein and into an aqueous solution of polyion, said polyion being charged oppositely to said protein, to thereby prepare a structurally controlled ultrathin protein film having a precise thickness controlled at a molecular level on said porous solid support, said porous support being capable of separating said substrate and products of the chemical reaction of said substrate;

initiating a chemical change of substrate molecules by containing the substrate with said immobilized protein thin film; and separating the substrate and the products of the chemical reaction of the substrate.

2. A method for a chemical reaction of substrate molecules comprising preparing an immobilized protein ultrathin film reactor composed of multiple layers of protein on a porous solid support by (a) immersing a porous solid support with an electrically charged surface into an aqueous solution of a first polyion or a first protein, said first polyion and said first protein being charged oppositely to said surface of said solid support, to reverse the surface charge of said porous solid support, (b) then immersing the porous solid support from (a) into an aqueous solution of a second polyion or a second protein, said second polyion and said second protein being charged oppositely to said surface of said solid support from (a) to reverse the surface charge of said porous solid support from (a), (c) optionally, repeating (a) and (b), and (d) preparing an ultrathin film in which at least two proteins are assembled; and initiating a chemical change of substrate molecules using the immobilized protein ultrathin film reactor.

3. A method for a chemical reaction of substrate molecules comprising immobilizing a protein thin film on a porous support by (a) immersing a porous solid support with an electrically charged surface into an aqueous solution of a first polyion or a first protein, said first polyion and said first protein being charged oppositely to said surface of said solid support, to reverse the surface charge of said solid support, (b) then immersing the porous solid support from (a) into an aqueous solution of a second polyion or a second protein, said second polyion and said second protein being charged oppositely to said surface of said porous solid support from (a) to reverse the surface charge of said solid support from (a), (c) optionally, repeating (a) and (b), and (d) preparing an ultrathin film in which at least two proteins are assembled, said porous support being capable of separating said substrate and products of the chemical reaction of said substrate;

contacting a substrate with said immobilized protein thin film; and separating the substrate and the products of the chemical reaction of the substrate.

4. A method for a chemical reaction of substrate molecules comprising preparing an immobilized enzyme ultrathin film reaction composed of multiple layers of enzyme of a porous solid support by immersing a porous solid support alternately into an aqueous solution of enzyme and into an aqueous solution of polyion, said polyion being charged oppositely to said enzyme to thereby prepare a structurally controlled ultrathin protein film having a precise thickness controlled at a molecular level onto said porous solid support; and initiating a chemical change of substrate molecules using the immobilized protein ultrathin film reactor.

5. The method for a chemical reaction of a substrate molecule according to claim 1, wherein the protein is an enzyme.

6. The method for a chemical reaction of a substrate molecule according to claim 2, wherein the protein is an enzyme.

7. The method for a chemical reaction of a substrate molecule according to claim 3, wherein the protein is an enzyme.

* * * * *